United States Patent [19]
Yahiaoui et al.

[11] Patent Number: 5,814,567
[45] Date of Patent: Sep. 29, 1998

[54] DURABLE HYDROPHILIC COATING FOR A POROUS HYDROPHOBIC SUBSTRATE

[75] Inventors: Ali Yahiaoui, Roswell; Xin Ning, Alpharetta; Charles Edward Bolian, II, Buford; Debra Jean McDowall, Roswell; David Charles Potts, Dunwoody; Daniel Joseph VanHout, Roswell, all of Ga.

[73] Assignee: Kimberly-Clark Worldwide, Inc., Neenah, Wis.

[21] Appl. No.: 665,172

[22] Filed: Jun. 14, 1996

[51] Int. Cl.$^6$ .................................................. B32B 3/26
[52] U.S. Cl. ...................... 442/118; 428/304.4; 428/903
[58] Field of Search .................. 442/118; 428/304.4, 428/903

[56] References Cited

U.S. PATENT DOCUMENTS

| | | | |
|---|---|---|---|
| 4,009,037 | 2/1977 | Mann et al. | 96/87 |
| 4,136,218 | 1/1979 | Nischwitz et al. | 427/339 |
| 4,144,886 | 3/1979 | Holst et al. | 128/284 |
| 4,200,558 | 4/1980 | Holst et al. | 260/17 A |
| 4,601,911 | 7/1986 | Ueno et al. | 427/34 |
| 4,649,026 | 3/1987 | Postle et al. | 422/56 |
| 4,668,359 | 5/1987 | Postle et al. | 204/182.7 |
| 4,777,046 | 10/1988 | Iwakura et al. | 424/435 |
| 5,147,343 | 9/1992 | Kellenberger | 604/368 |
| 5,294,478 | 3/1994 | Wanek et al. | 428/218 |

FOREIGN PATENT DOCUMENTS

| | | |
|---|---|---|
| 0111795A2 | 1/1983 | European Pat. Off. . |
| 0104608A1 | 9/1983 | European Pat. Off. . |
| 0388547A1 | 3/1989 | European Pat. Off. . |
| 6-2191569 | 8/1987 | Japan . |
| 2-6848 | 1/1990 | Japan . |
| 1213858 | 3/1968 | United Kingdom . |
| 1312431 | 1/1971 | United Kingdom . |

OTHER PUBLICATIONS

Copy of Search Report for PCT/US/97/09756 dated Oct. 23, 1997.

Japanese Abstract 63/301234 dated Aug. 12, 1988.

"Fabrication of a Continuous Wettability Gradient by Radio Frequency Plasma Discharge" by W. G. Pitt, Journal of Colliod and Interface Science, vol. 133, No. 1, Nov. 1989, pp. 223–227.

"A Wettability Gradient Method for Studies of Macromolecular Interactions at the Liquid/Solid Interface" by Elwing et al., Journal of Colloid and Interface Science, vol. 119, No. 1, Sep. 1987, pp. 203–210.

"A New Technique to prepare Gradient Surfaces Using density Gradient Solutions" by Golander et al., Colloids and Surfaces, 42 (1989) pp. 165–172.

(List continued on next page.)

*Primary Examiner*—James J. Bell
*Attorney, Agent, or Firm*—William E. Maycock

[57] ABSTRACT

A coated porous substrate composed of a hydrophobic polymer which is substantially uniformly coated with a hydrophilic polymeric material. The substrate may be a sheet-like material, examples of which are foams, fibers, and fibrous webs. The fibrous webs desirably will be nonwoven webs. The coating on the substrate is durable to an aqueous medium at a temperature in a range of from about 10° C. to about 50° C. and does not significantly suppress the surface tension of an aqueous medium with which the coated substrate may come in contact. The hydrophobic polymer may be a polyolefin, such as polyethylene or polypropylene. The hydrophilic polymeric material with which the polymer fibers are coated may be a polysaccharide or a modified polysaccharide. Also provided is a method of preparing a coated porous substrate which involves providing a porous substrate composed of a hydrophobic polymer. At least a portion of the substrate then is exposed to a field of reactive species. At least a portion of the porous substrate, including the portion exposed to the reactive species, is treated with a mixture which includes water and a hydrophilic polymeric material under conditions sufficient to substantially uniformly coat the porous substrate with the hydrophilic polymeric material.

15 Claims, 3 Drawing Sheets

OTHER PUBLICATIONS

"Spatially Resolved Adsorption Kinetics of Immunoglobulin G onto the Wettability Gradient Surface" by V. Hlady, Applied Spectroscopy, vol. 45, No. 2, 1991, pp. 246–252.

"Wettability Gradient Surfaces Prepared By Corona Discharge Treatment" by Lee et al., The 17$^{th}$ Annual Meeting of the Society for Biomaterials, May 1–5, 1991, Scottsdale, AZ, USA, p. 133.

"Hydrophobicity Gradient on Silica Surfaces: A Study Using Total Internal Reflection Fluorescence Spectroscopy" by Hlady et al., Colloids and Surfaces, 25 (1987), pp. 185–190.

"Gradient Surface Modifications Of Nonwovens For Controlled Wettability" by A. Yahiaoui et al., 10$^{th}$ Kimberly–Clark Technical Conference, Sep. 10–13, 1995.

DURABLE HYDROPHILIC COATING FOR A POROUS HYDROPHOBIC SUBSTRATE

BACKGROUND OF THE INVENTION

The present invention relates to a coated polymer substrate.

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polymers, however, where their hydrophobic nature either limits their usefulness or requires some effort to modify the surface characteristics of the shaped articles made therefrom. By way of example, polyolefins, such as polyethylene and polypropylene, are used to manufacture polymeric fabrics which are employed in the construction of such disposable absorbent articles as diapers, feminine care products, incontinence products, training pants, wipes, and the like. Such polymeric fabrics often are nonwoven webs prepared by, for example, such processes as meltblowing, coforming, and spunbonding. Frequently, such polymeric fabrics need to be wettable by water or aqueous-based liquids. Wettability can be obtained by spraying or otherwise coating (i.e., surface treating or topically treating) the fabric with a surf actant solution during or after its formation, and then drying the web.

Some of the more common topically applied surfactants are nonionic surfactants, such as polyethoxylated octylphenols and condensation products of propylene oxide with propylene glycol, by way of illustration only. These surfactants are effective in rendering normally hydrophobic polymeric fabrics water wettable. However, the surfactant is readily removed from the fabric, often after only a single exposure to an aqueous liquid. Such surfactants are effective in rendering the hydrophobic polymeric fabric wettable by lowering the surface tension of the aqueous liquid. Such a mechanism must involve at least partial removal of surfactant from the surfaces of the fibers of which the fabric is composed.

Accordingly, there is a need for a coated porous hydrophobic substrate having a durable coating which is wettable by water without significantly lowering the surface tension of an aqueous medium to which the coated substrate may be exposed.

SUMMARY OF THE INVENTION

The present invention addresses some of the difficulties and problems discussed above by providing a coated substrate composed of a hydrophobic polymer. The surfaces of the substrate are substantially uniformly coated with a hydrophilic polymeric material. The hydrophobic polymer may be, by way of illustration only, a polyolefin. For example, the polyolefin may be polyethylene or polypropylene.

The coating of the hydrophilic polymeric material is durable to an aqueous medium at a temperature in a range of from about 10° C. to about 50° C. Moreover, the coating of the hydrophilic polymeric material does not significantly suppress the surface tension of an aqueous medium with which the substrate may come in contact. In certain embodiments, the hydrophilicity of the coating of polymeric material will vary in a controlled manner across at least one dimension of the substrate.

By way of example, the substrate may be a sheet-like material, such as a sheet of a foamed material. The sheet-like material also may be a fibrous web, such as a woven or nonwoven fabric or web. The fibrous web desirably will be a nonwoven web.

Also by way of example, the hydrophilic polymeric material may be a polysaccharide. As another example, the polymeric material may be a modified polysaccharide. When the hydrophilic polymeric material is a polysaccharide, it may have a plurality of hydrophobic groups and a plurality of hydrophilic groups. The hydrophobic groups may be =CH— and —CH$_2$— groups in the polysaccharide backbone. The hydrophobic groups may be adapted to provide an affinity of the polymeric material for the hydrophobic polymer of which the porous substrate is composed and the hydrophilic groups may be adapted to render the polymeric material hydrophilic.

When the polymeric material is a modified polysaccharide, the hydrophobic groups may be =CH— and —CH$_2$— groups in the polysaccharide backbone or pendant groups. The hydrophilic groups also may be pendant groups. For example, the modified polysaccharide may be, by way of example only, a modified cellulose. For example, the hydrophobic groups may be pendant monovalent alkyl groups, such as ethyl groups. As another example, the hydrophilic groups may be pendant monovalent hydroxyalkyl groups, such as hydroxyethyl groups.

The coated porous substrate of the present invention may be used as a component of a disposable absorbent product. Examples of disposable absorbent products include, by way of illustration only, diapers; training pants; feminine care products, such as sanitary napkins and tampons; incontinent care products; surgical gowns; surgical drapes; wipes; and the like.

The present invention also provides a method of preparing a coated porous substrate which involves providing a porous hydrophobic polymer substrate and exposing at least a portion of the substrate to a field of reactive species. At least a portion of the substrate, including the portion exposed to a field of reactive species, then is treated with a mixture which includes water and a hydrophilic polymeric material as described above under conditions sufficient to substantially uniformly coat the surfaces of the porous substrate with the hydrophilic polymeric material. The coating of the hydrophilic polymeric material is durable to an aqueous medium at a temperature in a range of from about 10° C. to about 50° C. and the coating does not significantly depress the surface tension of an aqueous medium with which the coated porous substrate may come in contact. For example, the surface tension depression of such an aqueous medium may be less than about 10 percent.

The field of reactive species may be, for example, a corona field. The field of reactive species also may be, again by way of example, a plasma field. The strength of the field of reactive species may vary in a controlled manner across at least one dimension of the substrate.

If desired, subsequent to treating at least a portion of the porous substrate with the mixture comprising water and a hydrophilic polymeric material, a portion of the substrate may be exposed to a field of reactive species as described above.

DETAILED DESCRIPTION OF THE INVENTION

Figure 1:
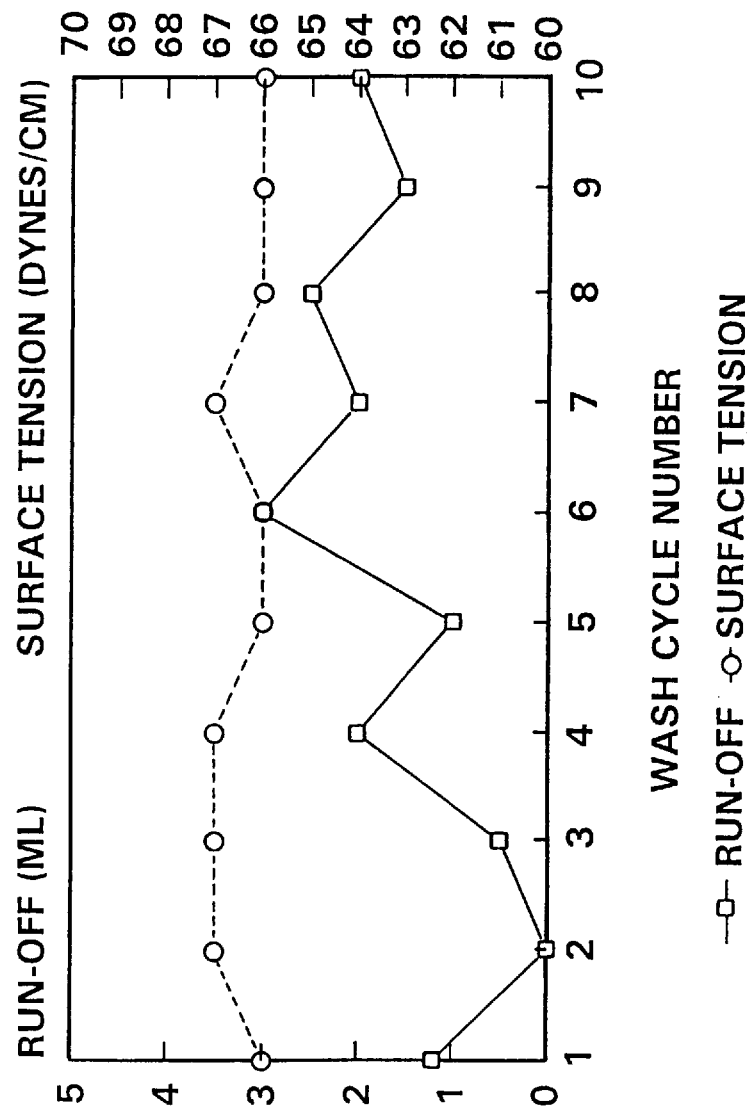
FIG. 1 is a plot of run-off in ml and surface tension of the run-off liquid in dynes/cm, respectively, versus wash cycle number for a nonwoven fabric coated in accordance with the present invention.

As used herein, the term "porous hydrophobic polymer substrate" is meant to include any shaped article, provided it is porous and composed, in whole or in part, of a hydrophobic polymer. For example, the substrate may be a sheet-like material, such as a sheet of a foamed material. The sheet-like material also may be a fibrous web, such as a woven or nonwoven fabric or web. The substrate also may include hydrophobic polymer fibers, per se, or hydrophobic polymer fibers which have been formed into a fibrous web. The fibrous web desirably will be a nonwoven web, such as, but not limited to, a meltblown web or a spunbonded web. The substrate also may be a laminate of two or more layers of a sheet-like material. For example, the layers may be independently selected from the group consisting of meltblown webs and spunbonded webs. However, other sheet-like materials may be used in addition to, or instead of, meltblown and spunbonded webs. In addition, the layers of the laminate may be prepared from the same hydrophobic polymer or different hydrophobic polymers.

The term "hydrophobic polymer" is used herein to mean any polymer resistant to wetting, or not readily wet, by water, i.e., having a lack of affinity for water. Examples of hydrophobic polymers include, by way of illustration only, polyolefins, such as polyethylene, poly(isobutene), poly (isoprene), poly(4-methyl-1-pentene), polypropylene, ethylene-propylene copolymers, ethylene-propylene-hexadiene copolymers, and ethylene-vinyl acetate copolymers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly (chlorotrifluoroethylene),chlorotrifluoroethylene-tetrafluoroethylene copolymers, poly(hexafluoropropylene), poly(tetrafluoroethylene), tetrafluoroethylene-ethylene copolymers, poly(trifluoroethylene), poly(vinyl fluoride), and poly(vinylidene fluoride); vinyl polymers, such as poly (vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly (heptafluoroisopropoxypropylene), and poly (methacrylonitrile); acrylic polymers, such as poly(n-butyl acetate), poly(ethyl acrylate), poly[(1-chlorodifluoromethyl) tetrafluoroethyl acrylate], poly[di(chlorofluoromethyl) fluoromethyl acrylate], poly (1,1-dihydroheptafluorobutyl acrylate), poly (1,1-dihydropentafluoroisopropyl acrylate), poly (1,1-dihydropentadecafluorooctyl acrylate), poly (heptafluoroisopropyl acrylate), poly[5-(heptafluoroisopropoxy)pentyl acrylate], poly[11-(heptafluoroisopropoxy)undecyl acrylate], poly[2-(heptafluoropropoxy)ethyl acrylate], and poly (nonafluoroisobutyl acrylate); methacrylic polymers, such as poly(benzyl methacrylate), poly(n-butyl methacrylate), poly(isobutyl methacrylate), poly(t-butyl methacrylate), poly (t-butylaminoethyl methacrylate), poly (dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly (1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); and polyesters, such a poly (ethylene terephthalate) and poly (butylene terephthalate)

The term "polyolefin" is used herein to mean a polymer prepared by the addition polymerization of one or more unsaturated monomers which contain only carbon and hydrogen atoms. Examples of such polyolefins include polyethylene, polypropylene, poly(1-butene), poly(2-butene), poly(1-pentene), poly(2-pentene), poly(3-methyl-1-pentene), poly(4-methyl-1-pentene), and the like. In addition, such term is meant to include blends of two or more polyolefins and random and block copolymers prepared from two or more different unsaturated monomers. Because of their commercial importance, the most desired polyolefins are polyethylene and polypropylene.

The hydrophobic polymer also may contain minor amounts of additives as is customary in the art. For example, the hydrophobic polymer may contain pigments, delustrants, antioxidants, antistatic agents, stabilizers, oxygen scavengers, and the like.

The term "durable" as used herein with reference to a coating of a hydrophilic polymeric material on the porous substrate means that the coated porous substrate remains wettable after at least three exposures to an aqueous medium, such as water, saline, and urine and other body fluids.

One procedure for evaluating durability when the porous substrate is a fibrous web is a modified run-off test followed by washing and drying (a wash/dry cycle). The fibrous web typically will remain wettable for at least five cycles of exposing, washing, and drying. Desirably, the coated porous substrate will remain wettable after being subjected to at least ten cycles.

The run-off test (exposure) and wash/dry procedure are described in U.S. Pat. No. 5,258,221 to Meirowitz et al. which is incorporated herein by reference. Typically, a generally rectangular, 8-inch by 15-inch (about 20-cm by 38-cm) sample of a fibrous web, such as a nonwoven web, is mounted on top of an absorbent core composed of polypropylene, wood pulp fibers, and/or a superabsorbent material. The resulting test assembly is centered on the inclined surface and held in place with tape at each corner of the assembly. The angle of the inclined surface is 45° instead of the 30° angle described in the patent. The funnel is located at approximately 7.8 inches (about 200 mm) from the bottom or lower edge of the test assembly. The valve of the funnel is located approximately 10 mm above the top surface of the test assembly. One hundred ml of water having a temperature of 35° C. is placed in the funnel. The valve of the funnel is opened to dispense the water over a period of about 15 seconds. The amount of water which runs off and is collected in the collection means is determined and recorded. A fibrous web is typically considered to pass the modified run-off test if the amount of water collected in the collection means is less than an amount deemed appropriate for a given type of fibrous web. For example, when the fibrous web is a lightweight (e.g., having a basis weight of 0.6 ounces per square yard or about 20 grams per square meter) spunbonded nonwoven web, the amount of water collected should be less than 20 ml.

The wash/dry cycle was modified by utilizing 500 ml, rather than one liter, of room-temperature water (about 23° C.). Thus, the generally rectangular sample of coated porous substrate described above is placed in the 500 ml of water. The sample is allowed to remain in the water for one minute while being agitated at 15–20 revolutions per minute by a mechanical shaker. The sample is removed from the water and excess liquid squeezed back into the wash water container. The sample is allowed to air dry overnight and then is subjected to the modified run-off test described above. This process is repeated the desired number of times. The surface tension of the wash water is determined after each wash/dry cycle with fresh water being used for each cycle. The surface tension of the water is determined according to ASTM Test Method D 1590-60 using a Fisher tensiometer (Fisher Scientific Company, Pittsburgh, Pa.).

As used herein, the term "hydrophilic polymeric material" means that the polymeric material has a surface free energy such that the polymeric material is wettable by an aqueous medium. That is, an aqueous medium wets the hydrophilic polymeric material with which the porous substrate is coated. For example, the surface free energy of the hydrophilic polymeric material may be at least about 50 dynes $cm^{-1}$. As another example, the surface free energy of the hydrophilic polymeric material may be in a range of from about 50 to about 72 dynes $cm^{-1}$.

The term "aqueous medium" is used herein to mean any liquid medium of which water is a major component. Thus, the term includes water per se and aqueous solutions and dispersions. For example, the aqueous medium may be a liquid bodily discharge, such as urine, menses, and saliva.

As used herein, the term "wettable" and variations thereof means wettable by an aqueous medium, i.e., the aqueous medium spreads over the surface of a substrate. The term is used interchangeably with the term "wettable by water" and variations thereof and has the same meaning.

As used herein, the phrase "affinity of the polymeric material for the porous hydrophobic polymer substrate" means that the hydrophilic polymeric material coats the substrate substantially uniformly (i.e., to an extent sufficient to permit the coated substrate to be wet by an aqueous medium), typically after first exposing the substrate to a field of reactive species. The term "partial affinity" means that the polymeric material partially coats the porous substrate. The functional consequence of a partial affinity is that the coated porous substrate is only partially wettable.

The term "monovalent alkyl group" is used herein to mean a monovalent alkyl group having from 1 to about 6 carbon atoms. Examples of monovalent alkyl groups include, by way of illustration only, methyl, ethyl, 1-propyl, isopropyl, 1butyl, 2-butyl, t-butyl, 1-pentyl, 2-pentyl, 3-pentyl, 2methyl-2-butyl, 3-methyl-2-butyl, 1-hexyl, 2-hexyl, 3-hexyl, 4-hexyl, 2,2 dimethylbutyl, 2,3-dimethylbutyl, 2-methylpentyl, 3-methylpentyl, 3-ethyl-2-butyl, and the like.

As used herein, the term "monovalent hydroxyalkyl group" means a monovalent alkyl group as described above in which a hydrogen atom has been replaced with a hydroxy group. Examples of monovalent hydroxyalkyl groups include, also by way of illustration, hydroxyethyl, 2-hydroxypropyl, 3hydroxypropyl, 1-hydroxy-2-propyl, 4-hydroxybutyl, 3-hydroxybutyl, 2-hydroxybutyl, 4-hydroxy-2-butyl, 3-hydroxy-2-butyl, 2-hydroxymethyl-2-propyl, 5-hydroxypentyl, 4-hydroxypentyl, 3-hydroxypentyl, 2-hydroxypentyl, 5-hydroxy-2-pentyl, 4hydroxy-2-pentyl, 3-hydroxy-2-pentyl, 5-hydroxy-3-pentyl, 4hydroxy-3-pentyl, 2-hydroxymethyl-2-butyl, 3-hydroxymethyl2-butyl, 3-methyl-1-hydroxy-2-butyl, 6-hydroxyhexyl, 4hydroxy-2-hexyl, 1-hydroxy-3-hexyl, 2-hydroxy-4-hexyl, 2,2-dimethyl-4-hydroxybutyl, 2,3-dimethyl-1-butyl, 2-hydroxymethylpentyl, 2-methyl-4-hydroxypentyl, 3-(2-hydroxyethyl)2-butyl, and the like.

The term "pendant" is used herein with respect to the monovalent alkyl and hydroxyalky groups to mean that such groups are attached to the polymer backbone but are not part of it. Thus, removal of the pendant groups will not alter the chemical structure of the backbone.

As already stated, the coated porous substrate of the present invention may include hydrophobic polymer fibers. Such fibers are substantially uniformly coated with a hydrophilic polymeric material. As an example, the hydrophobic polymer fibers may be polyolefin fibers. For example, the polyolefin fibers may be polyethylene or polypropylene fibers.

The hydrophobic polymer fibers generally may be prepared by any known means. As a practical matter, however, the fibers usually will be prepared by a melt-extrusion process and formed into a fibrous web, such as a nonwoven web. The term "melt-extrusion process" as applied to a nonwoven web is meant to include a nonwoven web prepared by any melt-extrusion process for forming a nonwoven web in which melt-extrusion to form fibers is followed by web formation, typically concurrently, on a foraminous support. The term includes, among others, such well-known processes as meltblowing, coforming, spunbonding, and the like. By way of illustration only, such processes are exemplified by the following references:

(a) meltblowing references include, by way of example, U.S. Pat. No. 3,016,599 to R. W. Perry, Jr., U.S. Pat. No. 3,704,198 to J. S. Prentice, U.S. Pat. No. 3,755,527 to J. P. Keller et al., U.S. Pat. No. 3,849,241 to R. R. Butin et al., U.S. Pat. No. 3,978,185 to R. R. Butin et al., and U.S. Pat. No. 4,663,220 to T. J. Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973);

(b) coforming references include U.S. Pat. No. 4,100,324 to R. A. Anderson et al. and U.S. Pat. No. 4,118,531 to E. R. Hauser; and (c) spunbonding references include, among others, U.S. Pat. No. 3,341,394 to Kinney, U.S. Pat. No. 3,655,862 to Dorschner et al., U.S. Pat. No. 3,692,618 to Dorschner et al., U.S. Pat. No. 3,705,068 to Dobo et al., U.S. Pat. No. 3,802,817 to Matsuki et al., U.S. Pat. No. 3,853,651 to Porte, U.S. Pat. No. 4,064,605 to Akiyama et al., U.S. Pat. No. 4,091,140 to Harmon, U.S. Pat. No. 4,100,319 to Schwartz, U.S. Pat. No. 4,340,563 to Appel and Morman, U.S. Pat. No. 4,405,297 to Appel and Morman, U.S. Pat. No. 4,434,204 to Hartman et al., U.S. Pat. No. 4,627,811 to Greiser and Wagner, and U.S. Pat. No. 4,644,045 to Fowells.

Other methods for preparing nonwoven webs are, of course, known and may be employed. Such methods include air laying, wet laying, carding, and the like. In some cases it may be either desirable or necessary to stabilize the nonwoven web by known means, such as thermal point bonding, through-air bonding, and hydroentangling. In addition to nonwoven webs, the hydrophobic polymer fibers may be in the form of continuous filaments or staple fibers, as well as woven or knitted fabrics prepared from such continuous filaments or staple fibers.

The coating of hydrophilic polymeric material is durable to an aqueous medium at a temperature in a range of from about 10° C. to about 50° C. and does not significantly suppress the surface tension of an aqueous medium with which the fibrous web may come in contact. For example, the surface tension of the aqueous medium may not be suppressed or lowered more than about 10 percent.

By way of illustration only, the hydrophilic polymeric material may be a polysaccharide. The polysaccharide may have a plurality of hydrophobic groups and a plurality of hydrophilic groups. The hydrophobic groups may be =CH— and —CH$_2$— groups in the polysaccharide backbone. The hydrophobic groups may be adapted to provide an affinity of the polymeric material for the hydrophobic polymer of which the porous substrate is composed and the hydrophilic groups may be adapted to render the polymeric material hydrophilic. Examples of polysaccharides include, for example, natural gums, such as agar, agarose, carrageenans, furcelleran, alginates, locust bean gum, gum arabic, guar gum, gum konjac, and gum karaya; microbial fermentation products, such as gellan gum, xanthan gum, and dextran gum; cellulose, such as microcrystalline cellulose; and animal products, such as hyaluronic acid, heparin, chitin, and chitosan.

Again by way of illustration only, the hydrophilic polymeric material may be a modified polysaccharide. A modified polysaccharide also may have a plurality of hydrophobic groups and a plurality of hydrophilic groups. The hydrophobic groups may be =CH— and —CH$_2$— groups in the polysaccharide backbone, or pendant groups. The hydrophilic groups also may be pendant groups. Again, the hydrophobic groups may be adapted to provide an affinity of the polymeric material for the hydrophobic polymer of which the porous substrate is composed and the hydrophilic groups may be adapted to render the polymeric material hydrophilic. By way of illustration only, examples of modified polysaccharides include modified celluloses or cellulose derivatives, such as hydroxyethyl cellulose,. hydroxypropyl cellulose, methyl cellulose, ethyl cellulose, methyl hydroxypropyl cellulose, ethyl hydroxyethyl cellulose, and carboxymethyl cellulose; starch and pectin derivatives, such as carboxymethyl starch, starch aldehyde, and pectates; and animal product derivatives, such as carboxymethyl chitin and carboxymethyl chitosan., Particularly useful types of polysaccharides and modified polysaccharides include, by way of illustration, agar; alginates; and modified celluloses, such as ethyl hydroxyethyl cellulose. In modified polysaccharides, particularly in the useful type of modified polysaccharides just noted, the hydrophobic groups may be pendant monovalent alkyl groups. For example, such hydrophobic groups may be methyl or ethyl groups. As a further example, the hydrophilic groups may be pendant monovalent hydroxyalkyl groups. As yet another example, such hydrophilic groups may be hydroxyethyl groups.

Finally, the hydrophilicity of the coating of polymeric material may vary in a controlled manner across at least one dimension of the coated porous substrate. For example, a coated porous substrate may have a central region of higher hydrophilicity which extends, for example, along the length of the substrate, with regions of lower hydrophilicity on both sides of the central region. Thus, the hydrophilicity of such a substrate would vary in a controlled manner across the width thereof. Other variations coming within the scope of the present invention will be readily apparent to those having ordinary skill in the art.

Turning now to the method for preparing a coated porous substrate, it involves providing a porous hydrophobic polymer substrate and exposing at least a portion of the substrate to a field of reactive species. At least a portion of the substrate, including the portion exposed to the field of reactive species, then is treated with a mixture which includes water and a hydrophilic polymeric material as described above under conditions sufficient to substantially uniformly coat the surfaces of the porous substrate with the hydrophilic polymeric material. The coating of the hydrophilic polymeric material is durable to an aqueous medium at a temperature in a range of from about 10° C. to about 50° C. and the coating does not significantly depress the surface tension of an aqueous medium with which the coated porous substrate may come in contact. For example, the surface tension depression of such an aqueous medium may be less than about 10 percent. In some instances, it may be either helpful or necessary to crosslink the coating on the porous substrate to impart a desired level of durability.

The field of reactive species serves to increase the affinity of the hydrophilic polymeric material for the porous hydrophobic polymer substrate. The field of reactive species may be, by way of example, a corona field. As another example, the field of reactive species may be a plasma field.

Without wishing to be bound by theory, it is believed that exposure of the porous hydrophobic polymer substrate to a field of reactive species results in alterations of the surfaces of the substrate, thereby temporarily raising the surface energy of the substrate. This, in turn, allows the penetration of the treating solution into the porous substrate; that is, the porous substrate may be saturated with the treating solution.

Although exposure of the porous substrate to a field of reactive species is a desired method of temporarily raising the surface energy of the substrate, other procedures may be employed. For example, the porous substrate may be treated with ozone or passed through an oxidizing solution, such as an aqueous medium containing chromium trioxide and sulfuric acid. Care should be taken with such other procedures, however, to either prevent or minimize degradation of the porous substrate.

The strength of the field of reactive species may be varied in a controlled manner across at least one dimension of the fibrous web. Upon coating the porous substrate with the hydrophilic polymeric material, the extent or degree of hydrophilicity of the coating is directly proportional to the strength of the field. Thus, the hydrophilicity of the coating of polymeric material will vary in a controlled manner across at least one dimension of the fibrous web.

The strength of the field of reactive species is readily varied in a controlled manner by known means. For example, a corona apparatus having a segmented electrode may be employed, in which the distance of each segment from the sample to be treated may be varied independently. As another example, a corona apparatus having a gap-gradient electrode system may be utilized; in this case, one electrode may be rotated about an axis which is normal to the length of the electrode. Other methods also may be employed; see, for example, "Fabrication of a Continuous Wettability Gradient by Radio Frequency Plasma Discharge", W. G. Pitt, *J. Colloid Interface Sci.*, 133, No. 1, 223 (1989); and "Wettability Gradient Surfaces Prepared by Corona Discharge Treatment", J. H. Lee, et al., *Transactions of the 17th Annual Meeting of the Society for Biomaterials*, May 1–5, 1991, page 133, Scottsdale, Ariz.

If desired, at least a portion of the porous substrate may be exposed to a field of reactive species subsequent to treating at least a portion of the porous substrate with a mixture comprising water and a polymeric material. Such post-exposure typically increases the hydrophilicity of the coated porous substrate. Moreover, the strength of the field of reactive species in such post-exposure also may vary in a controlled manner across at least one dimension of the fibrous web as already described. Such post-exposure may even enhance the durability of the coating through crosslinking.

The present invention is further described by the examples which follow. Such examples, however, are not to be construed as limiting in any way either the spirit or the scope of the present invention.

EXAMPLE 1

A 0.6 ounce per square yard or osy (about 20 grams per square meter or gsm) polypropylene spunbond fabric (Fabric A) was exposed to a corona discharge under ambient conditions. The field strength of the corona was 24 watts/$ft^2$/min (about 1.6 Joules/$cm^2$). Immediately following the corona treatment, the fabric was dipped in a 0.25 percent by weight aqueous solution of ethyl hydroxyethyl cellulose (Bermocol E481, Akzo Nobel), referred to hereinafter as Coating A. After complete saturation of the fabric, indicated by a change in color from white to translucent, the fabric was nipped between two rubber rollers in an Atlas laboratory wringer at 10 lbs (about 4.5 kg) nip pressure. The coated fabric then was dried in an oven at 60° C. for about 30 minutes.

Water absorption of the coated fabric was tested qualitatively by placing water drops on the surface of the fabric. An instantaneous absorption was observed which indicated that the fabric was substantially uniformly coated with the ethyl hydroxyethyl cellulose (Coating A).

The coating on the fabric was tested for durability by subjecting the fabric to multiple exposures to water as described in the modified run-off test procedure. The data are summarized in Table 1. In addition to durability, the coatings of the present invention do not lower the surface tension of the liquid to which the coated fabric is exposed. To demonstrate that such is the case, the surface tension of the water run-off was measured after each cycle performed in the durability test described above. The results are included in Table 1.

TABLE 1

Summary of Run-Off/Wash Test Results

| Cycle No. | Run-Off (ml) | Surface Tension[a] |
|---|---|---|
| 0 | 0 | 67 |
| 1 | 1.2 | 66 |
| 2 | 0 | 67 |
| 3 | 0.5 | 67 |
| 4 | 2.0 | 67 |
| 5 | 1.0 | 66 |
| 6 | 3.0 | 66 |
| 7 | 2.0 | 67 |
| 8 | 2.5 | 66 |
| 9 | 1.5 | 66 |
| 10 | 2.0 | 66 |

[a]Surface tension of the wash water, in dynes/cm.

In order to better visualize the data in the table, they were plotted as run-off in ml (left y-axis) and surface tension of wash water (right y-axis), respectively, versus wash cycle number. The plot is shown as FIG. 1. The figure clearly indicates that ethyl hydroxyethyl cellulose-coated fabric is durable to multiple exposures of 100 ml of water.

By comparison, a fabric coated with a typical surf actant (e.g., a polyethoxylated octylphenol, Triton® X-102) will not perform well to multiple exposures since the surfactant is essentially washed off upon the first exposure to water. For example, a sample of virgin Fabric A was coated with Triton® X-102 and subjected to the modified run-off test procedure. The run-off prior to the first washing was 2 ml, whereas the run-off after the first washing was 90 ml.

FIG. 1 also shows that virtually no change in the surface tension of the wash water occurred. On the other hand, a significant drop in surface tension of the wash water is observed with a Triton® X-102 treated fabric. By way of example, the water from the first washing of the Triton® X-102 treated fabric had a surface tension of 54 dynes/cm, which is a drop of roughly 20 percent from the surface tension of the water used (see Table 1).

EXAMPLE 2

The coating procedure of Example 1 was repeated, except that two other nonwoven fabrics, Fabrics B and C, were utilized and another ethyl hydroxyethyl cellulose (EHM100, Akzo Nobel), referred to hereinafter as Coating B, also was employed. Fabric B was a spunbond web composed of 50/50, eccentric sheath/core bicomponent, 1.3 denier (0.14 tex) fibers. The core consisted of Type 3445 polypropylene (Exxon Chemical Americas, Houston, Tex. 77079) and the sheath consisted of Aspun® 6811A linear low density polyethylene (The Dow Chemical Company). Each component contained 2 percent by weight of Ampacet 41438 titanium dioxide. Fabric C was a 1.5 osy (about 51 gsm) meltblown web prepared from Himont PF015 polypropylene (Himont Incorporated, Wilmington, Del.).

The coated fabrics then were tested for their ability to wick water against gravity (the vertical wicking test). The test utilized a 4.5-cm×22.5-cm sample, with the longest dimension of the sample being parallel with the machine direction. The sample was placed on a graduated sample holder and hung from a slide which was suspended over a reservoir containing a saline solution. The slide was lowered into the saline solution until 2.5 cm of the sample was below the surface of the solution. A timer was started and the position of the wicking fluid front was observed and recorded as a function of time over a 30-minute period.

The results of the wicking test are summarized in Table 2. In this and some subsequent tables, "Coating Add-on" represents the amount of coating on the sample, expressed as a percentage of the dry weight of the sample. Because of the low amounts involved, coating add-on is a calculated value. The sample was weighed, treated with the aqueous solution of a hydrophilic polymeric material, and weighed again. Subtracting the dry weight from the wet weight gave the wet pick-up. Multiplying the wet pick-up by the concentration of the hydrophilic polymeric material in the treating solution gave the amount of hydrophilic polymeric material in the sample. That amount then was divided by the dry weight of the sample and the quotient multiplied by 100 to give coating add-on. Thus, Coating Add-on=[(100) (Wet Wt. - Dry Wt.) (Concn.)]/Dry wt.

TABLE 2

Summary of Wicking Behavior of Coated Fabrics

| Fabric | Coating | Coating Add-on[a] | Vertical Wicking Height (cm) | | |
|---|---|---|---|---|---|
| | | | 5 min. | 15 min. | 30 min. |
| B | — | — | 0.0 | 0.0 | 0.0 |
| B | B | 0.1 | 9.5 | 10.5 | 10.5 |
| B | B | 0.2 | 14.0 | 18.5 | 21.0 |
| B | A | 0.1 | 9.0 | 10.0 | 15.0 |
| B | A | 0.2 | 12.5 | 14.5 | 15.0 |
| C | — | — | 0.0 | 0.0 | 0.0 |
| C | B | 0.1 | 12.5 | 18.0 | 20.0 |
| C | B | 0.2 | 13.0 | 18.5 | 20.0 |
| C | A | 0.1 | 12.0 | 18.0 | 20.0 |
| C | A | 0.2 | 14.0 | 20.0 | 21.0 |

[a]Expressed as a percentage of sample dry weight.

The data in Table 2 indicate the coated fabrics wick water well. The data also indicate that it is possible to tailor the wicking behavior of a fabric for a specific application by selecting the appropriate coating material, add-on level, and web structure.

EXAMPLE 3

The fabric employed in this example was Fabric D, a 2.5-osy (about 85 gsm) spunbond nonwoven web in which the fibers were side-by-side bicomponent fibers. The components, which were present in approximately equal amounts, consisted of the polyethylene and polypropylene utilized for Fabric B (Example 2). The fabric was cut into a sample 8 inches (about 20 cm) by 10 inches (about 25 cm). The sample was oxidized in a Branson/IPC Model PM119 plasma treater at 80 watts of power in an air plasma at 0.6 torr for 5 minutes. The sample then was immersed for about 30 seconds in a solution consisting of 3.97 g of calcium chloride dihydrate (Catalog No. 22,350-6, Aldrich Chemical Company, Milwaukee, Wis.) and 3,000 ml of water. The solution contained 0.1 percent by weight of calcium chloride. Excess solution was removed from the wetted fabric by vacuum extraction (i.e., passing the wetted fabric over a slot to which a vacuum was applied). The sample contained approximately 150 percent by weight wet pick-up (based on the dry weight of the sample) of the calcium chloride solution after vacuum extraction.

The still wet sample was dipped for about 30 seconds in a solution composed of 3.00 g or 0.1 percent by weight of high viscosity sodium alginate (Catalog No. A-7128, Sigma Chemical Company, St. Louis, Miss.) in 3,000 ml of water for about 30 seconds. Excess solution was removed from the wet sample by vacuum extraction. The sample at this stage contained approximately 300 percent of both the calcium chloride and sodium alginate solutions, resulting in the formation of a calcium alginate gel (Coating C) on the fibers of the sample. The sample then was air dried over night at ambient temperature (about 20°–25° C.).

The treated sample exhibited vertical wicking heights of 6.5 cm and 9.0 cm and 5 min and 15 min, respectively, and a surface tension depression of less than 2 percent. Surface tension depression was evaluated by placing a 1-inch by 9-inch (about 2.5-cm by about 23-cm) strip of coated fabric in 80 ml of water for 30 min. The surface tension of the water then was measured and compared with that of pure water; the comparison was expressed as a percent change.

EXAMPLE 4

A 12-inch by 12-inch (about 30-cm by about 30-cm) sample of barrier grade polypropylene meltblown web (Fabric C) was oxidized in a plasma treater at 300 watts of power in an oxidizing plasma for 1 minute. The sample then was immersed in an aqueous solution of 0.3 percent by weight calcium chloride dihydrate for about 30 seconds. Excess solution was removed by passing the sample between the rolls of an Atlas laboratory wringer. The sample contained between 200 and 250 percent wet pick-up of the calcium chloride solution.

The still wet sample then was dipped in a solution of 0.5 percent by weight of sodium polygalacturonate (Catalog No. P-1879, Sigma Chemical Company) in water for about 30 seconds. Excess solution was removed by passing the sample between the rolls of an Atlas laboratory wringer as before. The sample now contained from 200 to 250 percent by weight of a mixture of the calcium chloride and sodium polygalacturonate solutions, resulting in the formation of a calcium polygalacturonate gel coating (Coating D). The sample was dried overnight at ambient temperature.

After the sample had dried, it was subjected to the vertical wicking test with saline solution. The solution reached a height of 11 cm in five minutes.

In the examples which follow (Examples 5–14), the coated fabrics were evaluated for vertical wicking of saline solution, for surface tension depression, and for run-off. Surface tension depression was evaluated as described in Example 3. The run-off and vertical wicking tests were carried out as described previously (Examples 1 and 2, respectively).

EXAMPLE 5

A 7-inch by 10-inch (about 18-cm by 25-cm) sheet of 1.5 osy (about 51 gsm) polypropylene meltblown web (Fabric C) was treated in a radio-frequency (RF) plasma generator (Branson/IPC Model PM119 plasma treater) at 50 watts of power and about 0.6 torr for 10 minutes under hydrogen peroxide. The hydrogen peroxide vapor was generated by placing a small beaker containing 30 percent aqueous hydrogen peroxide solution (Catalog No. 5240, Baxter Diagnostic Inc., McGaw, Ill.) in the vacuum chamber of the plasma unit. The sheet then was dipped into a 0.2 percent by weight aqueous agarose solution (Coating E, Aldrich Chemical Co.) maintained at 70° C., and squeezed through an Atlas laboratory wringer to achieve a 100 percent by weight wet pick-up. The web, which was completely saturated in the bath, was dried under ambient conditions to a constant weight. The treated web exhibited vertical wicking heights of 13.5 cm and 20.5 cm at 5 min and 15 min, respectively, and a surface tension depression of 4 percent.

EXAMPLE 6

The procedure of Example 5 was carried out with Fabric B of Example 2; the fabric had a basis weight of 1.5 osy (about 51 gsm). The treated fabric exhibited vertical wicking heights of 14.5 cm and 18.0 cm at 5 min and 15 min, respectively, and a surface tension depression of 6 percent.

EXAMPLE 7

The procedure of Example 5 was repeated, except that the fabric was dipped into an aqueous solution containing 0.2 percent by weight of a 90:10 mixture by weight of agar (American Bio-organics Co.) and carrageenan (Kappa-Carrageenan, FMC Corporation) (Coating F). The fabric was completely saturated in the bath. The treated fabric exhibited vertical wicking heights of 13 cm and 19 cm at 5 min and 15 min, respectively, and a surface tension depression of 4 percent.

EXAMPLE 8

The procedure of Example 5 was repeated, except that the fabric was dipped into an aqueous solution containing 0.3 percent by weight of gellan gum (Coating G, Gelrite®, Kelco Co.). The fabric was completely saturated in the bath. The treated fabric exhibited vertical wicking heights of 7 cm and 11.5 cm at 5 min and 15 min, respectively, and a surface tension depression of 9 percent.

Upon replacing the gellan gum solution with a 0.2 percent by weight solution of locust bean gum (Coating H, LBG, Aldrich Chemical Co.), the treated fabric exhibited a vertical wicking height of 2 cm in 60 min, and a surface tension depression of 0 percent. Although the wicking result was not noteworthy, the coated web nevertheless was wettable and the coating was durable. Accordingly, locust bean gum is an example of a material which is not as hydrophilic as the other polymeric materials employed in the examples. However, locust bean gum provides a means for imparting moderate hydrophilic character to a porous hydrophobic polymer substrate.

The procedure was repeated with both Fabric B and Fabric C and a variety of coatings and add-on levels. Surface tension depression was evaluated as described in Example 3. The results are summarized in Table 3.

TABLE 3

Summary of Results

| Fabric | PT$^a$ | Coating Type | Add-On$^b$ | Wicking Ht. (cm) 5 min. | 15 min. | STD$^c$ |
|---|---|---|---|---|---|---|
| C | P$^d$ | I$^e$ | 0.1 | 10.0 | 16.5 | 8 |
| C | P | I | 0.5 | — | 19.0 | 5 |
| C | P | E$^f$ | 0.2 | 13.5 | 20.5 | 4 |
| C | P | F$^g$ | 0.2 | 13.0 | 19.0 | 4 |
| B | P | E | 0.2 | 14.5 | 18.0 | 6 |
| B | P | F | 0.2 | 13.0 | 19.0 | 0 |
| C | P | G$^h$ | 0.3 | 7.0 | 11.5 | 9 |
| B | P | G | 0.3 | 14.5 | 18.0 | 10 |

$^a$Pre-treatment.
$^b$Expressed as a percentage of sample dry weight.
$^c$Percent surface tension depression.
$^d$Plasma.
$^e$Agar.
$^g$Agar/carrageenan.
$^h$Gellan gum.

EXAMPLE 9

A treater at Faustel, Inc. (Germantown, Wis.) was used to continuously surface-treat a roll of 24-inch (about 61-cm) wide fabric. The fabric was passed sequentially through an Enercon RF Corona treater (tuned to about 20 watts/ft$^2$/min or about 1.3 Joules/cm$^2$ energy input), a dip-and-squeeze coater, and a through-air drying oven before rewinding. A 1.5 osy polypropylene meltblown web (Fabric C) was treated on-line at 15 ft/min. (about 7.6 cm/sec), wherein the coater contained a 0.3 percent by weight agar (Coating I, American Bio-Organics Co.) solution at 50° C., and drying was carried out at 40° C. The treated web exhibited vertical wicking heights of 5.5 cm and 8.5 cm at 5 min and 15 min, respectively, and 0 percent surface tension depression. Surface tension depression was evaluated as described in Example 3. The results are summarized in Table 4.

TABLE 4

Summary of Results

| Fabric | PT$^a$ | Coating Type | Add-On$^b$ | Wicking Ht. (cm) 5 min. | 15 min. | STD$^c$ |
|---|---|---|---|---|---|---|
| B | OC$^d$ | I$^e$ | 0.3 | 8.0 | 9.5 | 0 |
| C | OC | I | 0.3 | 9.0 | 12.5 | 0 |

$^a$Pre-treatment.
$^b$Expressed as a percentage of sample dry weight.
$^c$Percent surface tension depression.
$^d$On-line corona.
$^e$Agar.

EXAMPLE 10

A 7-inch by 10-inch (about 18-cm by 25-cm) sheet of 0.6 osy (about 20 gsm) polypropylene spunbond diaper liner (commercially produced at Kimberly-Clark Corporation's Berkeley mill) (Fabric A) was treated in a Branson Plasma generator for 5 minutes under hydrogen peroxide plasma as described in Example 3. The sheet then was dipped into a 0.3 percent by aqueous solution of agar (Coating I, American Bioorganics Co.) maintained at 70° C., and squeezed through an Atlas laboratory ringer to achieve a 100% wet pick-up. The web, which was completely wet out in the bath, was dried under ambient conditions. The treated liner showed no surface tension depression. The modified run-off test (Example 1) was conducted to examine the coating durability. The results are shown in Table 5 which follows Example 11.

EXAMPLE 11

The procedure of Example 10 was repeated, except that after the plasma treatment the sheet was sprayed with a hot, 0.3 percent by aqueous agar (Coating I, American Bio-organics Co.) solution using a laboratory glass sprayer to achieve approximately 100 percent by weight wet pick-up. The web was dried to constant weight under ambient conditions. The treated liner showed no surface tension depression. The treated liner was tested as described in Example 10. The results of the test for both Examples 10 and 11 are summarized in Table 5 (in the table, "Dip-and-Nip" refers to Example 10 and "Spray" refers to Example 11).

TABLE 5

Summary of Run-off Test Results

| Insult No. | Run-off (g) Dip-and-Nip | Spray |
|---|---|---|
| 1 | 0 | 0 |
| 2 | 0.3 | 0.4 |
| 3 | 0 | 1 |
| 4 | 0 | 0.7 |
| 5 | 0.1 | 1 |
| 6 | 0 | 2.3 |
| 7 | 0.4 | 2.5 |
| 8 | 0.2 | 1.2 |
| 9 | 0.6 | 1.2 |
| 10 | 0.2 | 2.9 |
| 11 | 0.6 | 5.1 |
| 12 | 0.8 | 0.4 |
| 13 | 1.7 | 1.2 |
| 14 | 0.6 | 2.1 |
| 15 | 1 | 0.7 |

15

EXAMPLE 12

A sheet of a metallocene polyolefin foam (OPCELL® LC31 foam, Sentinel Products Corp., Hyannis, Mass.) was cut to a thickness of 0.25 inch (about 0.6 cm). The foam was treated in a Plasma generator (Branson/PC Model PM119) at 80 Watts, 0.6 torr in an air plasma for 8 minutes. The foam then was saturated with a 0.2 percent by weight agar (Coating I) solution at approximately 60° C. The foam was vacuum extracted by passing it over a slot to which a vacuum was applied until an approximately 250 percent wet pick-up was achieved. All samples were air dried prior to testing. Drops of water placed on the foam absorbed into the structure within 1 minute, compared to untreated foam where the drop did not penetrate or spread at all, even after 15 minutes.

The amount of fluid the material would hold also was determined. The sample was placed in water under a 110 gram weight for 5 minutes (the weight was necessary as the samples were buoyant). The amount of water retained by the foam per gram of foam is listed in Table 6 at the end of Example 15. As seen in the table, the treated material held twice as much fluid as the untreated foam.

EXAMPLE 13

The procedure of Example 12 was repeated with agar (Coating I), except that the foam employed was a different metallocene polyolefin foam (OPCELL® LC33 foam, Sentinel Products Corp.). The foam was vacuum extracted until the wet pick-up was approximately 100 percent. The samples were air dried prior to testing. Drops of water placed on the foam absorbed into the structure within 0.5 minute compared to untreated foam where the drop did not penetrate or spread, even after 15 minutes. The amount of fluid contained in the foam was measured as described in Example 12 and is summarized in Table 6 which follows Example 15. The treated foam held more water than the untreated material.

EXAMPLE 14

The procedure of Example 12 was repeated, except that after the plasma treatment the foam was saturated with a 0.4 percent by weight aqueous solution of calcium chloride dihydrate. Excess solution was removed from the wetted foam by vacuum extraction until the wet weight was approximately 150 percent of the dry weight. The still wet foam then was dipped in a 0.3 percent by weight aqueous solution of high viscosity sodium alginate. Excess solution was removed from the wet foam by vacuum extraction until the total wet weight was 300 percent of the dry weight. The reaction product, calcium alginate gel (Coating C), was present in the foam at this point. The foam then was air dried overnight at ambient temperature. Drops of water placed on the foam went into the structure within 0.5 minute compared to untreated foam where the drop did not penetrate or spread, even after 15 minutes. The amount of fluid contained in the foam was measured and is summarized in Table 6 which follows Example 15. The treated foam held over 3 times as much water as the untreated material.

EXAMPLE 15

The foam of Example 13 was plasma treated as described in Example 12. The foam then was saturated with a 0.4 percent by weight aqueous solution of calcium chloride dihydrate. Excess solution was removed from the wetted foam by vacuum extraction until the wet weight was approximately 150 percent of the dry weight. The still wet foam then was dipped in a 0.3 percent by weight aqueous solution of high viscosity sodium alginate. Excess solution was removed from the wet foam by vacuum extraction until the total wet weight was 300 percent of the dry weight. The reaction product, calcium alginate gel (Coating C), was in the foam at this point. The foam then was air dried overnight at ambient temperature. Drops of water placed on the foam went into the structure instantly compared with untreated foam where the drop did not penetrate or spread, even after 15 minutes. The amount of fluid contained in the foam was measured and is summarized in Table 6, which follows. The treated foam held more water than the untreated material.

TABLE 6

Summary of Foam Treatment Results

| Foam | Coating | Fluid Retained |
|------|---------|----------------|
| LC31 | None | 2.57 |
| LC31 | I[a] | 6.20 |
| LC31 | C[b] | 9.04 |
| LC33 | None | 7.06 |
| LC33 | I | 11.91 |
| LC33 | C | 17.30 |

[a]Agar.
[b]Calcium alginate.

EXAMPLE 16

This example describes the use of a segmented electrode corona discharge to generate variable wettability zones on the same nonwoven fabric.

Figure 2:
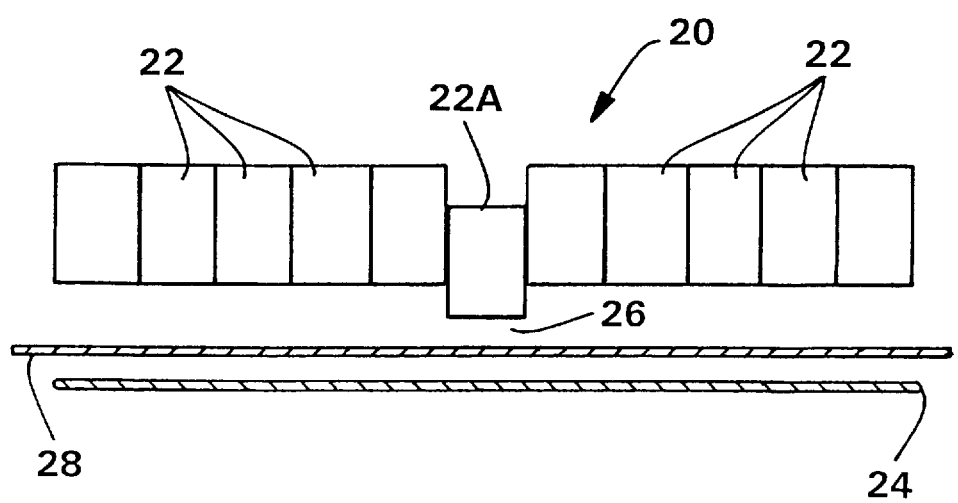
FIG. 2 is a diagrammatic representation of the segmented electrode of a segmented electrode corona discharge apparatus employed in an example.

A 1.5 osy (about 51 gsm) polypropylene meltblown fabric having a width of 14 inches (about 36 cm) (Fabric C) was coated with ethyl hydroxyethyl cellulose (Coating A) as described in Example 1. The coated fabric then was oxidized in a one inch zone along the length of the fabric; this was achieved by exposing the coated fabric to a corona discharge equipped with a segmented electrode (Flexydine System, Corotec Corporation, Farmington, Conn.) made of one-inch segments; the electrode is shown schematically in FIG. 2. In FIG. 2, a segmented electrode 20, viewed normal to the machine cross-direction, consists of a plurality of independent segments 22. The center segment 22A is located closer to the ground electrode 24 in order to provide a critical corona discharge gap 26. A coated fabric 28 separates the segmented electrode 20 from the ground electrode 24.

Figure 3:
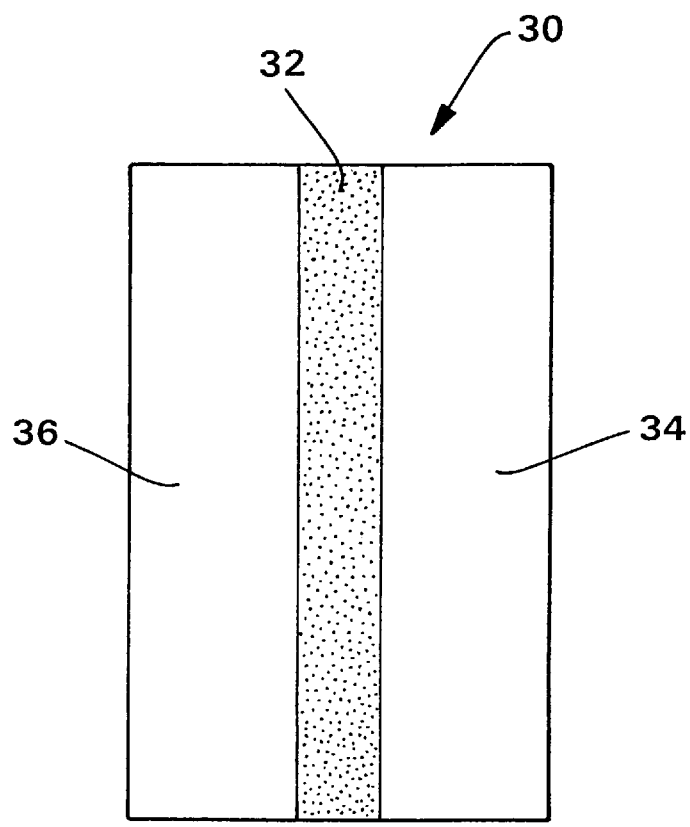
FIG. 3 is diagrammatic representation of a substrate having zones with different wettability and/or wicking characteristics.

A corona discharge was generated by activating the center electrode 22A (FIG. 2) at an energy input of 24 watts/ft$^2$/min (about 1.6 Joules/cm$^2$). This treatment generated a central zone which was significantly more wettable than the adjacent zones which had not been exposed to a corona discharge. The zones resulting from the corona discharge are shown diagrammatically in FIG. 3. In FIG. 3, the nonwoven web 30 has a central zone 32 and two side zones 34 and 36 extending the length of the fabric.

The wettability of the fabrics was assessed by measuring their ability to wick fluid against gravity (i.e., vertical wicking) as a function of time. The vertical wicking results are reported in Table 7.

TABLE 7

Vertical Wicking Data for Zoned,
Coated Polypropylene Nonwoven Webs

| Time (min) | Vertical Wicking Height (cm) | |
|---|---|---|
| | Central Zone | Side Zones |
| 1.5 | 7.0 | 4.0 |
| 3.0 | 10.0 | 5.0 |
| 5.0 | 12.0 | 7.0 |
| 9.0 | 14.5 | 7.0 |
| 10.0 | 15.0[a] | 8.0 |
| 15.0 | — | 9.0 |

[a]Maximum height.

As Table 7 clearly shows, the central zone (post-corona treated) wicks fluid higher and faster than the side zones.

For the purpose of measuring contact angles, the above procedure was repeated with polypropylene films in place of the nonwoven web. Measurements of contact angles on the films were preferable because the intrinsic wettability of these coatings can be compared more reliably, i.e., the effect of capillarity is not present in films as would be the case in nonwoven fabrics. The contact angle was measured using the sessile water drop method (see, e.g., "The contact Angle and Interface Energetics", J. D. Andrade, L. M. Smith, and D. E. Gregonis, in *Surface and Interfacial Aspects of Biomedical Polymers*, Vol. 1, edited by J. D. Andrade, 1985, Plenum Press, New York) and the results are reported in Table 8. Virgin film which had not been either coated or exposed to a corona discharge was used as a control.

TABLE 8

Water Contact Angles for Polypropylene Films
Coated with Ethyl Hydroxyethyl Cellulose

| Material | Contact Angle (°) |
|---|---|
| Control | 97 |
| Coated only (side zones) | 30 |
| Coated and corona treated (central zone) | 0 |

Table 8 demonstrates the improvements in wettability resulting from the coating of ethyl hydroxyethyl cellulose, and such coating combined with a post-corona treatment. The table also demonstrates the advantage in the post-corona treatment of the coated film.

Further, the effect of corona post-oxidation was elucidated by X-ray photoelectron spectroscopy (XPS) analysis of the surface of the nonwoven web. The results of the XPS analysis are reported in Table 9 as the oxygen/carbon ratio (O/C).

TABLE 9

XPS Data for Polypropylene Nonwoven Webs
Coated with Ethyl Hydroxyethyl Cellulose

| Material | O/C Atom-Percent Ratio |
|---|---|
| Control | 0.01 |
| Coated only (side zones) | 0.55 |
| Coated and corona treated (central zone) | 0.75 |

The above table shows that the O/C ratio was higher for the central zone which had been subjected to a corona discharge, compared to the side zones which had not been subjected to a corona discharge.

The contact angle, vertical wicking, and XPS data correlate well and clearly indicate that the higher the oxidation level of the surface, as measured by XPS, the lower the contact angle and the faster the vertical wicking rate. Most importantly, the wettability behavior as related to fluid transport (i.e., vertical wicking) can be controlled in specific zones on the same nonwoven fabric.

EXAMPLE 17

The procedure of Example 16 was repeated, except that the corona discharge was replaced with a radio-frequency glow discharge (RFGD). Typically, the coated fabric was placed between two movable aluminum sleeves so that a narrow zone about one inch (about 2.5 cm) wide was exposed to the RFGD under the following conditions:

Power=50 Watts

Pressure=0.5 torr

Gas=air

Exposure time=5 minutes

The vertical wicking results are summarized in Table 10.

TABLE 10

Vertical Wicking Data for Polypropylene Nonwoven
Webs Coated with Ethyl Hydroxyethyl Cellulose
With and Without a Post-RFGD Treatment

| Time (min) | Vertical Wicking Height (cm) | |
|---|---|---|
| | Central Zone | Side Zones |
| 1.5 | 6.0 | 3.5 |
| 3.0 | 8.5 | 4.5 |
| 5.0 | 12.0 | 7.0 |
| 10.0 | 15.0[a] | 9.0 |
| 15.0 | — | 11.5 |

[a]Maximum height.

Upon comparing the data in Table 10 with the data in Table 7, it is evident that the RFGD post-treatment was approximately equivalent to the corona discharge post-treatment.

EXAMPLE 18

A sample of Fabric C (the 1.5 osy, or 51 gsm, polypropylene meltblown web described in Example 2) was laminated to a sample of Fabric B (the spunbond web composed of sheath/core bicomponent fibers also described in Example 2). The two fabrics were coated as described in Example 1. While still saturated with the coating solution, the fabrics were placed together and the resulting sheet was passed through a laboratory wringer at a nip pressure of 10 lbs (about 4.5 kg) to remove excess coating solution. The laminate thus produced was allowed to dry in an oven until no further weight loss was observed, typically at 60° C. for 30 minutes. The laminate then was tested for vertical wicking and its performance was compared to that of samples of the individual coated fabrics of which the laminate was composed. The results are summarized in Table 11.

TABLE 11

Vertical Wicking Data for Each Nonwoven Web
and A Laminate of both Webs, All Being Coated
with Ethyl Hydroxyethyl Cellulose

| | Vertical Wicking Height (cm) | | |
|---|---|---|---|
| Time (min) | Laminate | Fabric B | Fabric C |
| 1.0 | 5.0 | 1.0 | 3.5 |
| 2.0 | 8.0 | 2.5 | 4.0 |
| 4.0 | 15.0 | 4.0 | 6.0 |

The laminate composed of both Fabrics B and C clearly provided superior wicking performance compared to the individual fabrics. Moreover, the performance of the laminate suggests that an unexpected synergism results from the combination of the two fabrics.

While the specification has been described in detail with respect to specific embodiments thereof, it will be appreciated that those skilled in the art, upon attaining an understanding of the foregoing, may readily conceive of alterations to, variations of, and equivalents to these embodiments.

What is claimed is:

1. A coated porous substrate which comprises:
   a porous hydrophobic polymer substrate which is substantially uniformly coated with a hydrophilic polymeric material in an amount of from about 0.1 to about 1.25 percent by weight, based on the dry weight of the substrate; in which
   the hydrophilic polymeric material is a polysaccharide or a modified polysaccharide;
   the coating of hydrophilic polymeric material is durable to an aqueous medium at a temperature in a range of from about 10° C. to about 50° C.; and
   the coating of hydrophilic polymeric material will not significantly suppress the surface tension of an aqueous medium with which the coated porous substrate may come in contact.

2. The coated porous substrate of claim 1, in which the porous hydrophobic polymer substrate is a porous sheet-like material.

3. The coated porous substrate of claim 2, in which the porous sheet-like material is selected from the group consisting of foams, fibers, and fibrous webs.

4. The coated porous substrate of claim 3, in which the porous sheet-like material is a fibrous web comprised of polyolefin fibers.

5. The coated porous substrate of claim 1, in which the hydrophilic polymeric material is crosslinked.

6. The coated porous substrate of claim 1, in which the modified polysaccharide is a modified cellulose.

7. The coated porous substrate of claim 1, in which the hydrophilicity of the coating of the hydrophilic polymeric material varies in a controlled manner across at least one dimension thereof.

8. A disposable absorbent product having as a component thereof the coated porous substrate of claim 1.

9. A disposable absorbent product having as a component thereof the coated porous substrate of claim 2.

10. A disposable absorbent product having as a component thereof the coated porous substrate of claim 4.

11. A disposable absorbent product having as a component thereof the coated porous substrate of claim 5.

12. A disposable absorbent product having as a component thereof the coated porous substrate of claim 6.

13. A disposable absorbent product having as a component thereof the coated porous substrate of claim 7.

14. A laminate which comprises at least two layers of the coated fibrous web of claim 4.

15. The laminate of claim 14, in which the layers are independently selected from the group consisting of meltblown webs and spunbonded webs.

* * * * *